US011764980B2

(12) United States Patent
Sun et al.

(10) Patent No.: US 11,764,980 B2
(45) Date of Patent: Sep. 19, 2023

(54) DIGITAL CONTACT TRACING SECURITY AND PRIVACY WITH PROXIMITY-BASED ID EXCHANGE WITH A TIME-BASED DISTANCE-BOUNDING

(71) Applicants: Sheng Sun, Ottawa (CA); Wen Tong, Ottawa (CA)

(72) Inventors: Sheng Sun, Ottawa (CA); Wen Tong, Ottawa (CA)

(73) Assignee: Huawei Technologies Co., Ltd., Shenzhen (CN)

( * ) Notice: Subject to any disclaimer, the term of this patent is extended or adjusted under 35 U.S.C. 154(b) by 239 days.

(21) Appl. No.: 17/246,421

(22) Filed: Apr. 30, 2021

(65) Prior Publication Data
US 2022/0360453 A1 Nov. 10, 2022

(51) Int. Cl.
*H04L 29/06* (2006.01)
*H04L 9/32* (2006.01)
(Continued)

(52) U.S. Cl.
CPC .......... *H04L 9/3271* (2013.01); *H04L 9/0643* (2013.01); *H04L 43/0864* (2013.01); *H04W 4/38* (2018.02); *G16H 50/80* (2018.01)

(58) Field of Classification Search
CPC . H04L 9/3271; H04L 9/0643; H04L 43/0864; H04L 63/06; H04L 63/061; H04L 63/065; H04L 63/068; H04L 63/10; H04L 63/107; H04L 63/20; H04L 63/205; H04W 4/38; H04W 12/02; H04W 12/04;
(Continued)

(56) References Cited

U.S. PATENT DOCUMENTS

| 2013/0102252 A1 | 4/2013 | Rasmussen et al. |
| 2019/0075461 A1* | 3/2019 | Sun ........................ H04L 9/0643 |
| 2022/0104008 A1* | 3/2022 | Luo ........................ H04W 12/02 |

FOREIGN PATENT DOCUMENTS

| CN | 1977257 A | 6/2007 |
| CN | 112042153 A | 12/2020 |

OTHER PUBLICATIONS

N. Ahmed et al., "A Survey of COVID-19 Contact Tracing Apps," in IEEE Access, vol. 8, pp. 134577-134601, 2020, doi: 10.1109/ACCESS.2020.3010226. (Year: 2020).*

(Continued)

*Primary Examiner* — Malcolm Cribbs (57) ABSTRACT

A method, system and devices for digital contact tracing security and privacy with proximity-based ID exchange with distance-bounding. The method is performed by a first wireless communication device and provides for exchanging IDs with a second wireless communication device. A rolling proximity identifier A associated with the first wireless communication device is sent to the second wireless communication device. A rolling proximity identifier B associated with the second wireless communication device is received from the second wireless communication device. A cryptographic challenge response authentication with time-based distance-bounding is performed based on a hash value determined from the rolling proximity identifiers in accordance with a hash function. The rolling proximity identifier of the second wireless communication device is only stored in memory in response to a successful cryptographic challenge response authentication.

19 Claims, 5 Drawing Sheets

(51) Int. Cl.
  *H04L 9/06* (2006.01)
  *H04W 4/38* (2018.01)
  *H04L 43/0864* (2022.01)
  *G16H 50/80* (2018.01)

(58) Field of Classification Search
  CPC ..... H04W 12/06; H04W 12/12; H04W 12/30; H04W 12/50; H04W 12/60; H04W 12/61; H04W 12/63; G16H 50/80; G06F 21/44; G06F 21/445; G06F 21/62; G06F 21/6245; G06F 21/6254
  See application file for complete search history.

(56) References Cited

OTHER PUBLICATIONS

Sarah Clarke, COVID-19 tracking apps raise privacy concerns in Asia, Al Jazeera Media Network, https://www.aljazeera.com/news/2020/05/covid-19-tracking-apps-raise-privacy-concerns-asia-200502081131364.html May 2020.

Guideline for Isolation Precautions: Preventing Transmission of Infectious Agents in Healthcare Settings (2007), III. Precautions to Prevent Transmission of Infectious Agents, Center for Disease Control and Prevention (CDC), https://www.cdc.gov/infectioncontrol/guidelines/isolation/precautions.html 2007.

Rob Sun, Edward Au, Yan Xin and Allan Chu, FTM Security with Distance Bounding Protoco, IEEE, 23 pages https://mentor.ieee.org/802.11/documents?is_dcn=distance%20bounding Nov. 2017.

Contact Tracing, Cryptography Specification Preliminary—Subject to Modification and Extension, https://blog.google/documents/56/Contact_Tracing_-_Cryptography_Specification.pdf Apr. 2020.

Contact Tracing, Bluetooth Specification, Preliminary—Subject to Modification and Extension, https://blog.google/documents/58/Contact_Tracing_-_Bluetooth_Specification_v1.1_RYGZbKW.pdf Apr. 2020.

Nick Steele, Balancing Privacy and Security: Google Apple Contact Tracing, Duo, https://duo.com/labs/research/balancing-privacy-and-security-google-apple-contact-tracing Jun. 25, 2020.

Krawczyk, P. Eronen, for Comments: 5869—HMAC-based Extract-and-Expand Key Derivation Function (HKDF) May 2010.

H. Krawczyk, M. Bellare, Request for Comments: 2104—HMAC: Keyed-Hashing for Message Authentication Feb. 1997.

\* cited by examiner

DIGITAL CONTACT TRACING SECURITY AND PRIVACY WITH PROXIMITY-BASED ID EXCHANGE WITH A TIME-BASED DISTANCE-BOUNDING

TECHNICAL FIELD

The present disclosure relates to security and privacy, and more specifically, to a digital contact tracing security and privacy with proximity-based ID exchange with a time-based distance-bounding.

BACKGROUND

In public health, contact tracing is the process of identifying persons who may have come into contact with an infected person having COVID-19 or other infectious disease ("contacts") and subsequent collection of further information about these contacts. By tracing the contacts of infected individuals, testing them for infection, treating the infected and tracing their contacts in turn, public health aims to reduce infections in the population.

Contact tracing applications are mobile software applications designed to aid contact tracing in response to the coronavirus pandemic. Contact tracing applications have been developed and deployed in many countries to fight the COVID-19 pandemic. However, security and privacy concerns exist with current contact tracing applications due to the potential for man-in-the-middle attacks, interception, spoofing, forgery attacks, replay attacks, pranking attacks and other vulnerabilities. For example, with COVID-19 relay pranking, some mobile devices can record and replay a "proximity identifier" through their mobile device to "prank" victims or, on a greater scale, causes panic in community.

In addition, current contact tracing applications have a high false positivity rate of disease-communicable contact proximity due to inaccuracies in the utilized distance measurements schemes by prior art methods due to Bluetooth transmission signal power or reliance on GPS data. For example, with respect to Bluetooth, contact is based on whether a user's mobile device comes within range of a mobile device of an infected person. However, the Bluetooth transmission signal power results in a range of about 100 meters from the user's mobile device, resulting in a high probability of a false positive.

Further, privacy breaching is a significant concern of current contact tracing applications even though popular contact tracing applications such apply randomized MAC addresses to conceal user identity due to the tracking of user location histories in a centralized repository, among other reasons.

Thus, there is a need for contact tracing solutions which address security and privacy concerns, and which provide more accurate proximity determinations, thereby reducing the false positivity rate of disease-communicable contact proximity.

SUMMARY

The present disclosure provides a method, system and devices for digital contact tracing security and privacy with proximity-based ID exchange with time-based distance-bounding. The method of the present disclosure provides a proximity-based exchange of identifiers with time-based distance-bounding which provides several advantageous. Firstly, the method is air interface neutral, meaning it can be used with Bluetooth™, Wi-Fi™, or both, and potentially other wireless communication protocols. Existing solutions rely upon Bluetooth™ or GPS for proximity discovery means. Secondly, the method provides privacy protection by anonymizing the identifier exchanged. Thirdly, the method protects against various attacks including man-in-the-middle attacks, replay attacks, forgery attacks, and pranking attacks. Lastly, the method reduces false positive readings of disease-communicable contact by ensuring the precision of distance at which proximity is detected, a distance of approximately of 10 meters or less (e.g., between 3 and 6 feet or between 1 and 2 m in some examples) in the method of the present disclosure compared with a distance of approximately 100 m or less with existing solutions.

Generally, the method of the present disclosure is performed by a first wireless communication device and provides for exchanging IDs with a second wireless communication device. After detecting the presence of the second wireless communication device, a rolling proximity identifier is exchanged with the second wireless communication device. A cryptographic challenge response authentication with time-based distance-bounding is performed based on a hash value determined from the rolling proximity identifiers in accordance with a hash function. The rolling proximity identifier of the second wireless communication device is only stored in memory in response to a successful cryptographic challenge response authentication.

In accordance with a first aspect of the present disclosure, there is provided a method performed by a first wireless communication device for exchanging identifiers (ID) with a second wireless communication device. A rolling proximity identifier A associated with the first wireless communication device is sent to the second wireless communication device. A rolling proximity identifier B associated with the second wireless communication device is received from the second wireless communication device. A cryptographic challenge response authentication with time-based distance-bounding is performed on the rolling proximity identifiers A and B. The cryptographic challenge response authentication with time-based distance-bounding is based on a hash value determined from the rolling proximity identifier A and the rolling proximity identifier B in accordance with a hash function. The rolling proximity identifier B is stored in memory in response to a successful cryptographic challenge response authentication.

In some or all examples of the first aspect, before the rolling proximity identifiers are exchanged, the first and second wireless communication devices are detected by each other via a first wireless communication protocol.

In some or all examples of the first aspect, the rolling proximity identifiers are exchanged using the first wireless communication protocol.

In some or all examples of the first aspect, the method further comprises, after storing the rolling proximity identifier B in memory, determining whether an amount of time has expired from a time at which the rolling proximity identifier B of the second wireless communication device was stored, and removing the rolling proximity identifier B of the second wireless communication device from memory in response to a determination that the amount of time has expired.

In some or all examples of the first aspect, the amount of time is an amount of isolation time set by a public health authority.

In some or all examples of the first aspect, the predetermined amount of time is between 7 and 21 days, in some examples 14 days.

In some or all examples of the first aspect, the method further comprises refraining from storing the rolling proximity identifier B in memory in response to an unsuccessful cryptographic challenge response authentication.

In some or all examples of the first aspect, the cryptographic challenge response authentication with time-based distance-bounding comprises: determining the hash value based on the rolling proximity identifier A and the rolling proximity identifier B in accordance with the hash function; generating a challenge bit; sending the challenge bit to the second wireless communication device; receiving a response bit from the second wireless communication device; determining whether the response bit matches the corresponding challenge bit in accordance with a check function; determining whether a round trip time for the challenge-response transmission exceeds a time threshold, wherein the time threshold is based on a proximity threshold, wherein the transmission begins with sending a challenge bit and ends with receiving a response bit; determining that the hash value has been verified in response to a determination that the round trip time for the challenge-response transmission does not exceed the time threshold and a determination that the response bit matches the challenge bit; and determining that the hash value has not been verified in response to a determination that the round trip time for the challenge-response transmission exceeds the time threshold or a determination that the response bit does not match the challenge bit.

In some or all examples of the first aspect, the hash function is performed on a concatenation of A and B, wherein the output of the hash function is truncated to 2n bits, wherein a0 is the first half of the output bits of the hash function, wherein a0 and a1 are each $\underline{n}$ bits in size.

In some or all examples of the first aspect, the response bit is based on the challenge bit, wherein the response bit has a value equal to a most significant bit of a0 when the challenge bit has a value of 0 and the response bit has a value equal to a most significant bit of a1 when the challenge bit has a value of 1.

In some or all examples of the first aspect, n is 4 such that 0.30 and a1 are each 4 bits in size.

In some or all examples of the first aspect, the cryptographic challenge response authentication with time-based distance-bounding comprises: determining the hash value based on the rolling proximity identifier A and the rolling proximity identifier B in accordance with the hash function; generating an n-bit random binary number C, where $\{C_1, C_2, \ldots C_n\}$, where $C_i \in (0,1)$, wherein each bit in the random binary number C represents a challenge bit; for each bit in the random binary number C: sending a challenge bit to the second wireless communication device; receiving a response bit from the second wireless communication device; determining a round trip time for the challenge-response transmission beginning with the sending of the challenge bit and ending with the receiving of the response bit; determining whether the round trip time exceeds a time threshold, wherein the time threshold is based on a proximity threshold, and determining whether the response bit matches the challenge bit in accordance with a check function based on the hash value; determining that the hash value has been verified in response to a determination that the round trip time for the challenge-response transmission does not exceed the time threshold and a determination that the response bit matches the challenge for each challenge bit in the random binary number C; and determining that the hash value has not been verified in response to a determination that the round trip time for the challenge-response transmission exceeds the time threshold or a determination that the response bit does not match the challenge bit for any challenge bit in the random binary number C.

In some or all examples of the first aspect, the proximity threshold is a physical or social distance set by a public health authority.

In some or all examples of the first aspect, the proximity threshold is between 3 and 6 feet or between 1 and 2 m.

In some or all examples of the first aspect, the hash function is performed on a concatenation of A and B, wherein the output of the hash function is truncated to 2n bits, wherein a0 is the first half of the output bits of the hash function, wherein a0 and a1 are each n bits in size.

In some or all examples of the first aspect, the response bit is based on the challenge bit, wherein the response bit has a value equal to a most significant bit of a0 when the challenge bit has a value of 0 and the response bit has a value equal to a most significant bit of a1 when the challenge bit has a value of 1.

In some or all examples of the first aspect, the hash function is SHA-256, wherein the output of the SHA-256 hash function is truncated to 2n bits.

In some or all examples of the first aspect, n is 4 such that a0, a1 and the random binary number C are each 4 bits in size.

In some or all examples of the first aspect, the first wireless communication protocol is Bluetooth.

In some or all examples of the first aspect, the first wireless communication protocol is Wi-Fi.

In accordance with another aspect of the present disclosure, there is provided a wireless communication device comprising a processor, a memory and a communication subsystem. The memory having tangibly stored thereon executable instructions for execution by the processor. The executable instructions, in response to execution by the processor, cause the wireless communication device to perform the methods described above and herein.

In accordance with a further aspect of the present disclosure, there is provided a non-transitory machine-readable medium having tangibly stored thereon executable instructions for execution by a processor of a wireless communication device. The executable instructions, in response to execution by the processor, cause the wireless communication device to perform the methods described above and herein.

Other aspects and features of the present disclosure will become apparent to those of ordinary skill in the art upon review of the following description of specific implementations of the application in conjunction with the accompanying figures.

DETAILED DESCRIPTION OF EXAMPLE EMBODIMENTS

The present disclosure is made with reference to the accompanying drawings, in which embodiments are shown. However, many different embodiments may be used, and thus the description should not be construed as limited to the embodiments set forth herein. Rather, these embodiments are provided so that this application will be thorough and complete. Wherever possible, the same reference numbers are used in the drawings and the following description to refer to the same elements, and prime notation is used to indicate similar elements, operations or steps in alternative embodiments. Separate boxes or illustrated separation of functional elements of illustrated systems and devices does not necessarily require physical separation of such functions, as communication between such elements may occur by way of messaging, function calls, shared memory space, and so on, without any such physical separation. As such, functions need not be implemented in physically or logically separated platforms, although they are illustrated separately for ease of explanation herein. Different devices may have different designs, such that although some devices implement some functions in fixed function hardware, other devices may implement such functions in a programmable processor with code obtained from a machine-readable medium. Lastly, elements referred to in the singular may be plural and vice versa, except where indicated otherwise either explicitly or inherently by context.

Figure 1:
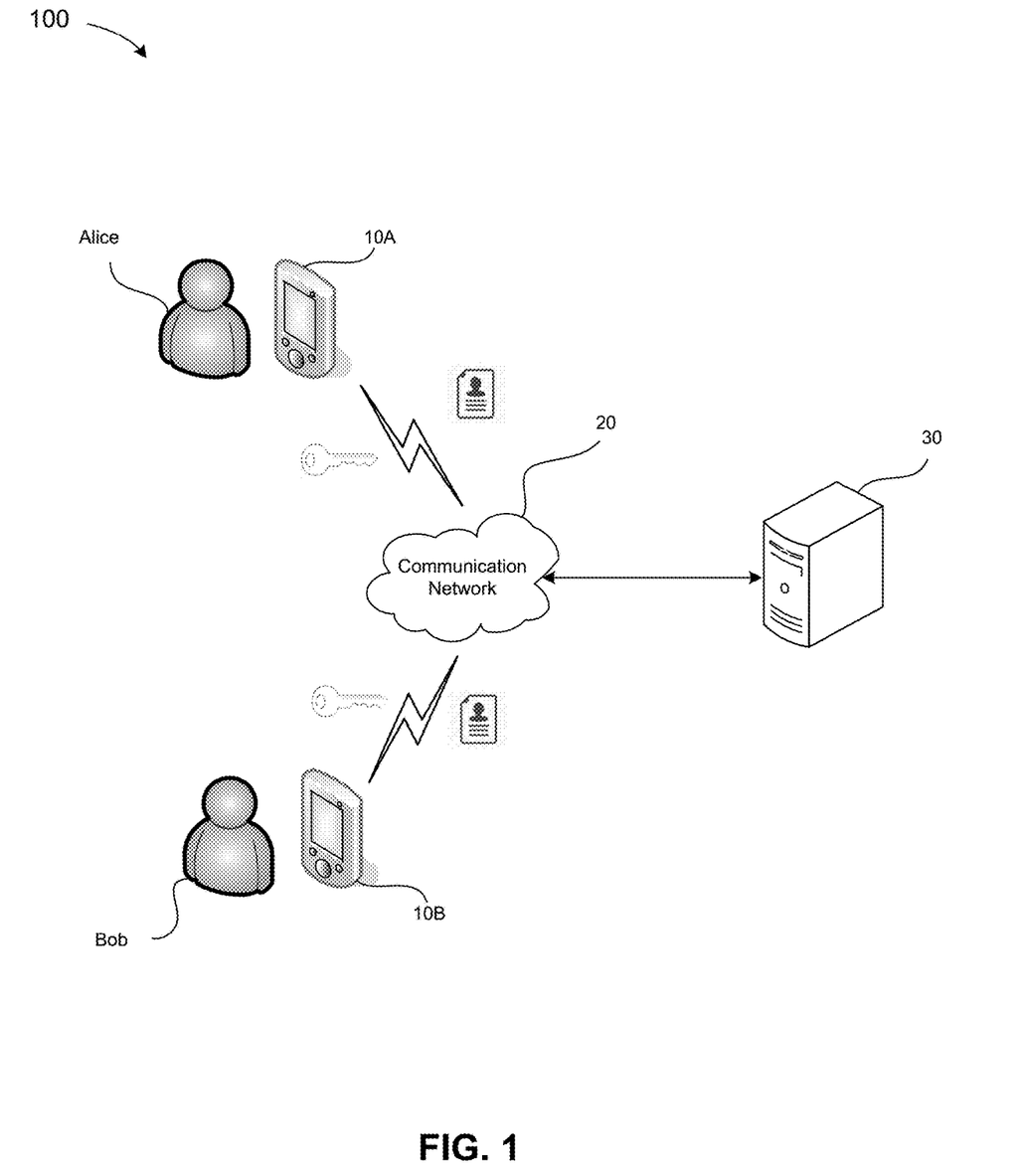
FIG. 1 is a schematic block diagram of a wireless communication system suitable for performing digital contact tracing in accordance with the present disclosure.

FIG. 1 illustrates a wireless communication system ("communication system") 100 in accordance with an example embodiment of the present disclosure. The communication system 100 comprises a plurality of wireless communication devices ("wireless devices") 10 associated with respective users, a communication network 20, and a server 30. In the shown embodiment, wireless device 10A is associated with a user "Alice" and wireless device 10B is associated with a user "Bob". The wireless devices 10 communicate with each other using a wireless communication protocol such as Bluetooth™ or Wi-Fi™. Depending on the wireless communication protocol, the wireless devices 10 may communicate directly with each other or indirectly with each other via a communication network 20 such as the Internet. A wireless communication protocol other than Bluetooth™ or Wi-Fi™ may be used in other embodiments. Other possible wireless communication protocols may include IEEE 802.11, IEEE 802.15.3a (also referred to as UltraWideband (UWB)), Z-Wave, ZigBee, and infrared (e.g., such as an Infrared Data Association (IrDA) communications).

The wireless devices 10 communicate with the server 30 via the communication network 20. The server 30 may be located behind a firewall (not shown) to secure the server 30 and the connection between the server 30 and the wireless devices 10. The wireless devices 10 communicate securely with the server 30, for example, using Transport Layer Security (TLS) or its predecessor Secure Sockets Layer (SSL). TLS and SSL are cryptographic protocols which provide communication security over the Internet. TLS and SSL encrypt network connections above the transport layer using symmetric cryptography for privacy and a keyed message authentication code (MAC) for message reliability. In response to TSL or SSL being used, cryptographic keys for such communication are typically stored in a persistent memory 112 of the wireless devices 10.

The server 30 is an application server that may comprise one or more server modules. The server 30 manages data and notifications for a contact tracing application 160 (FIG. 2) installed on the wireless devices 10. Contact tracing data for users and their wireless devices 10 are stored by the server 30 in a database (not shown). The database stores contact information in the form of contact identifiers (IDs) of other users of the contact tracing application 160 that a given user been in close contact with (i.e., other users that the given user has been within a predetermined proximity threshold of). The contact information stored by the wireless devices 10 and server 30 is anonymous and does not publicly expose the name or other personal information of the users. To track the contact information of a user of the contact tracing application 160, the user must consent the sharing of their information, for example, as part of the application installation or setup procedure.

Figure 3:
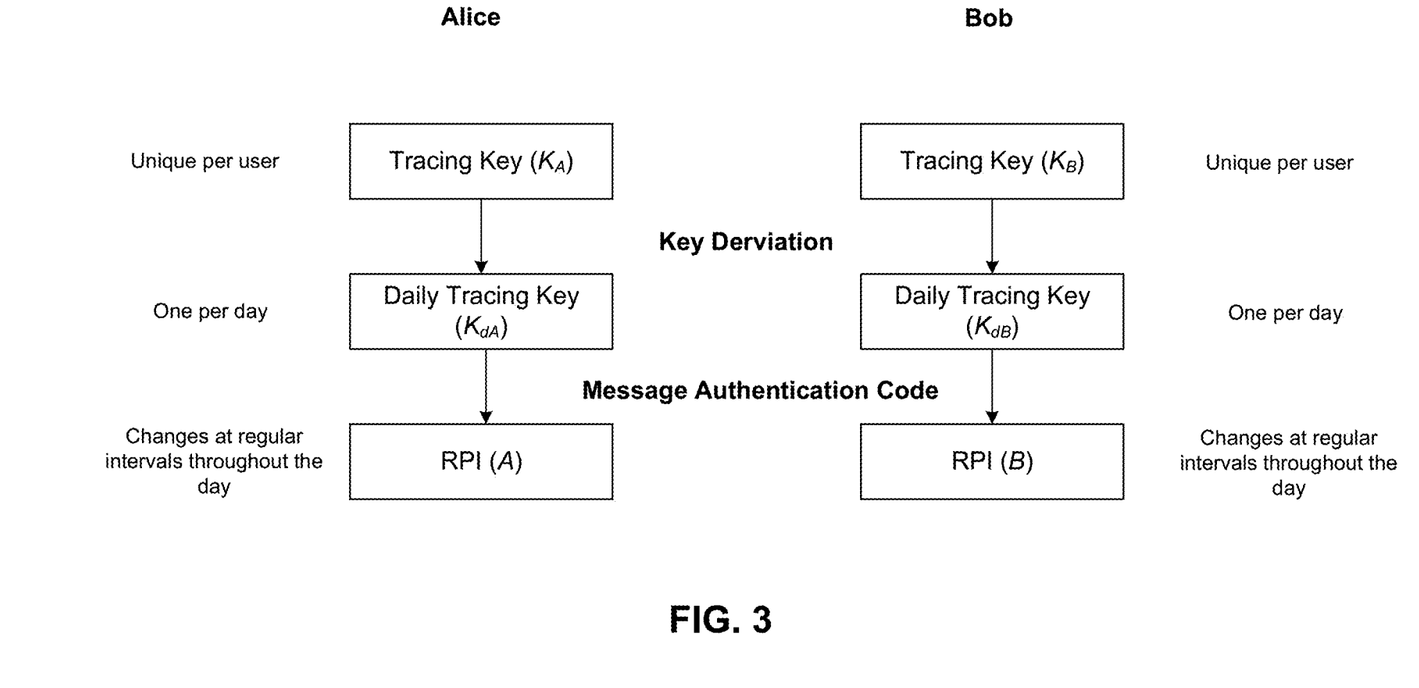
FIG. 3 is schematic block diagram of digital contact tracing key architecture in accordance with an example embodiment of the present disclosure.

Referring to FIG. 3, a digital contact tracing key architecture for tracking the contact information of users in accordance with an example embodiment of the present disclosure will be described. Each user of the contact tracing application 160 is assigned a unique per user permanent tracing key K which acts as a secure, anonymous identifier. The permanent tracing key assigned to Alice and Bob are denoted $K_A$ and $K_B$, respectively. The permanent tracing keys are generated and provided to the wireless device 10 of each user using a suitable key generation protocol or scheme, examples of which are known in the art and outside of the scope of the present disclosure. For example, a cryptographic random number generator may be used to generate the permanent tracing key. The key generation protocol or scheme used to generate the permanent tracing keys is set by the contact tracing application 160 so that all permanent tracing keys are generated using the same key generation protocol. The tracing keys $K_A$ and $K_B$ are stored in the persistent memory 112 of the wireless devices 10A and 10B respectively, typically in secure or protected memory of the persistent memory 112 which cannot be accessed directly or indirectly by a user. The tracing keys are generated and stored during an initially setup of the contact tracing application 160 or the wireless device 10. The permanent tracing key is not shared or exchanged. The permanent tracing key may be a 32-byte key in some examples.

The permanent tracing key is used to generate a temporary tracing key, such as a daily tracing key $K_d$, for the respective user. The daily tracing key is generated for each 24-hour period. The temporary tracing key also acts as a secure, anonymous identifier similar to the permanent tracing key but by changing regularly, provides additional privacy for the user and protection against various attacks and vulnerabilities. The daily tracing keys for Alice and Bob are denoted $K_{dA}$ and $K_{dB}$ respectively, and are stored in the persistent memory 112 of the wireless devices 10A and 10B respectively, typically in secure or protected memory of the persistent memory 112 with the permanent tracing keys $K_A$ and $K_B$. The daily tracing keys are generated from the permanent tracing keys $K_A$ and $K_B$ using a suitable key generation protocol or scheme, examples of which are known in the art and outside of the scope of the present disclosure. For example, the daily tracing key may be generated from the permanent tracing key by the Hashed Message Authentication Code (HMAC)-based key derivation function (HKDF) function as defined by IETF RFC 5869 using the Secure Hash Algorithm (SHA)-256 hash function, the content of which is incorporated herein by reference. The key generation protocol used to generate the daily tracing keys is set by the contact tracing application 160 so that all daily tracing keys are generated using the same key generation protocol.

The daily tracing key is not shared or exchanged unless data providing an indication of a positive test result for an infectious disease in respect of a user of the wireless device 10 is received by the contact tracing application 160. The data providing an indication of a positive test result for an infectious disease in respect of a user may be in the form of user input received by the contact tracing application 160 or a message received by the wireless device 10, such as from the server 30. The daily tracing key may be a 16-byte key in some examples. The use of 16-byte keys yields a low probability of false positives while keeping storage requirements on the wireless devices 10 and server 30 low.

A rolling proximity identifier (RPI) is generated at regular intervals for each user at a predetermined frequency, for example, every 15 minutes. The RPI is a privacy-preserving identifier that is exchanged with other wireless devices 10 that come within a predetermined proximity threshold in accordance with the method 400 described below and acts as the contact ID. The RPIs for Alice and Bob are denoted A and B, respectively, and are stored in the persistent memory 112 of the wireless devices 10A and 10B respectively, typically in secure or protected memory of the persistent memory 112 with the permanent tracing keys $K_A$ and $K_B$ and daily tracing keys $K_{dA}$ and $K_{dB}$. The RPI is generated from the daily tracing key and a time indication such as a time internal number or other suitable time indication. The RPI is a random binary number generated by a cryptographic hash function or other suitable means. Examples of suitable hash functions are well known in the art such as the SHA-256 hash function, the detail of which are outside of the scope of the present disclosure. For example, the RPI may be generated by the HMAC function as defined by IETF RFC 2104, using the SHA-256 hash function, the content of which is incorporated herein by reference. The hash function used to generate the RPI is set by the contact tracing application 160 so that all RPIs are generated using the same hash function. The RPI may be a 16-byte identifier in some examples. The use of 16-byte identifiers yields a low probability of collisions and limits the risk of false positive matches while keeping storage requirements on the wireless devices 10 low.

The RPI may be broadcast by the wireless device 10 over one or more wireless communication protocols such as Bluetooth™ and Wi-Fi™. Each RPI received by a wireless device 10 from another wireless devices 10 is stored in persistent memory 112, such as protected memory of the persistent memory 112. Each RPI may be stored in association with a date stamp associated with a date on which the respective RPI was received and stored in the persistent memory 112. The RPI of other wireless devices 10 may be stored in a contact tracing log. The RPI of other wireless devices 10 are stored for a predetermined amount of time after which the RPIs are removed or deleted from persistent memory 112. The predetermined amount of time that the RPIs are stored may be determined by a public health authority, which may be between 7 and 21 days in some examples, in some examples 14 days.

In response to receiving data indicating a positive test result for an infectious disease in respect of a user of the wireless device 10, the daily tracing keys for a threshold number of days that the respective user may have been infected are determined by the wireless device 10. The subset of daily tracing keys for the threshold number of days that the respective user may have been infected are referred to as diagnosis keys (or temporary exposure keys). The threshold number of days may be set by a public health authority, which may be between 7 and 21 days in some examples, in some examples 14 days. The diagnosis keys associated with the diagnosis keys for the respective user are then uploaded from the respective wireless device 10 to the server 30 over Internet.

The server 30 regularly receives diagnosis keys for users who have received a positive test result for an infectious disease has been received via the contact tracing application 160 installed on the wireless devices 10 of the respective users. Typically, the diagnosis keys are sent to the server 30 immediately upon the contact tracing application 160 receiving data indicating a positive test result for an infectious disease in respect of a user of the wireless device 10.

Wireless devices 10 having the contact tracing application 160 installed thereon periodically downloads the diagnosis keys of users who have tested positive for an infectious disease in one or more geographic regions designated by the user throughout the day, for example every 15 minutes. The diagnosis keys of users who have tested positive for an infectious disease in one or more geographic regions designated by the user may be broadcast by the server 30 throughout the day, for example every 15 minutes. The geographic regions may be defined by a radius from a designated location, such as a home or work, which may be defined by street addresses provided by the user. The geographic regions are akin to a geofence around the designated location. The size of the radius or geofence may be defined by a public health authority, user or application provider.

In response to receiving the diagnosis keys for users who have positive for an infectious disease in one or more geographic regions designated by the user (the "positive users"), the contact tracing application 160 uses the diagnosis keys to generate all possible RPIs that may have been broadcasted throughout a given day. This amounts to 144 RPIs that could have been broadcasted throughout a given day when broadcast every 15 minutes. Each of the possible RPIs is compared against the list of RPIs in the contact tracing log stored locally on the wireless device 10.

In response to a match being found, a first notification is generated on the wireless device 10. The first notification is typically a visual notification in the form of a message displayed on a display of the wireless device 10. A sound or audible notification may accompany the display of the message contemporaneously. A second notification with additional information for the user about what to do next may be subsequently provided, for example, in the form of a further message displayed on a display of the wireless device 10. Because the RPI is anonymized, the user does not know what other user was diagnosed only that the user was in the vicinity of another user who was recently diagnosed with an infectious disease and roughly how long the user was exposed.

The above-described communication system 100 is provided for the purpose of illustration only. The above-described communication system 100 includes one possible communication network configuration of a multitude of possible configurations. Suitable variations of the communication system 100 will be understood to a person of skill in the art and are intended to fall within the scope of the present disclosure. The teachings of the present disclosure are flexible and capable of being operated in various different environments without compromising any major functionality. In some embodiments, the communication system 100 includes multiple components distributed among a plurality of computing devices. One or more components may be in the form of machine-executable instructions embodied in a machine-readable medium.

Figure 2:
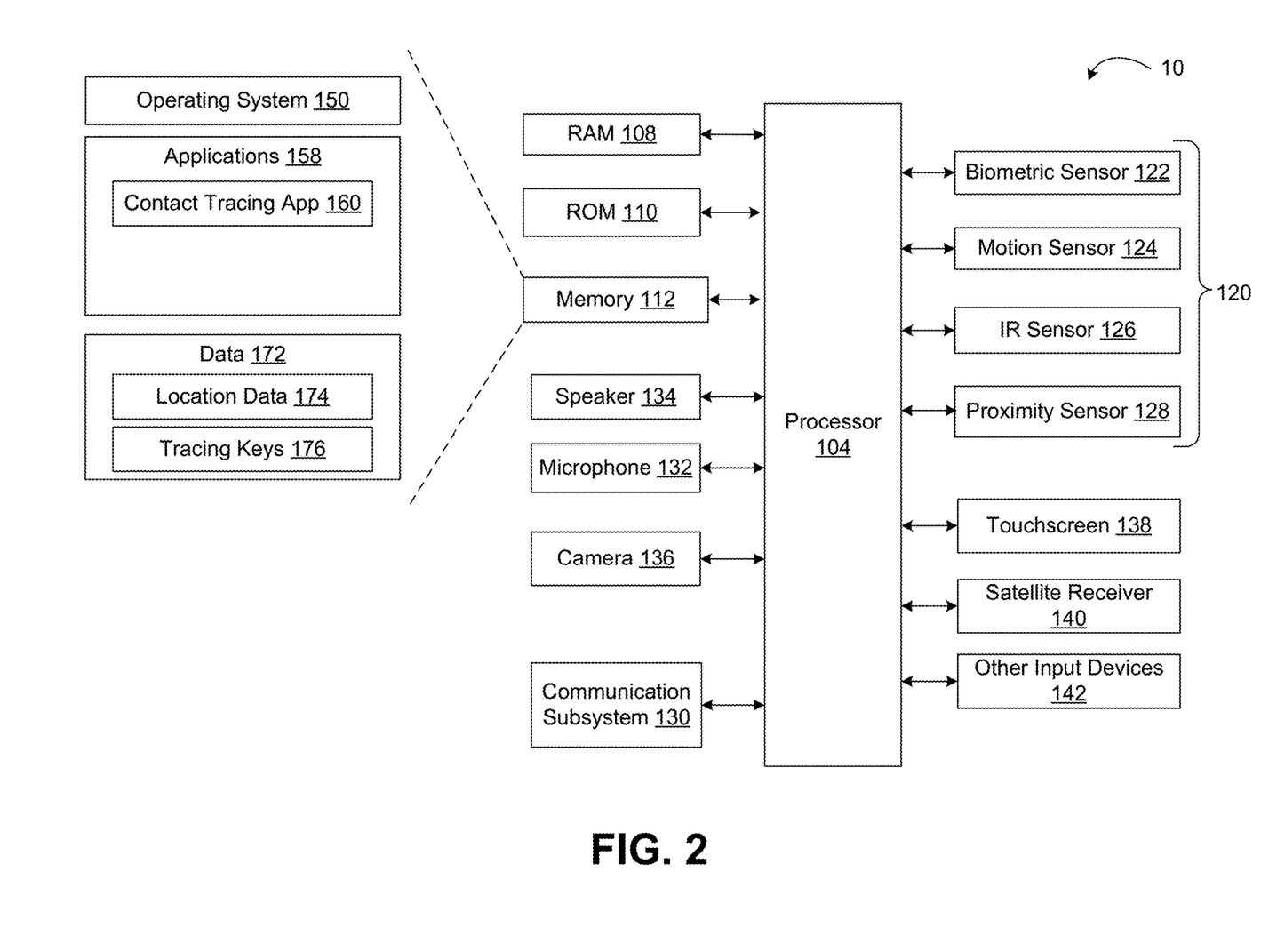
FIG. 2 is a block diagram of an example wireless communication device suitable for practicing the teachings of the present disclosure.

Reference is next made to FIG. 2 which illustrates a wireless device 10 suitable for practicing the teachings of the present disclosure. Examples of the wireless device 10 include, but are not limited to, a smartphone or tablet. The wireless device 10 includes a processing system comprising a processor 104 (such as a microprocessor or central processing unit (CPU)) which controls the overall operation of the wireless device 10. The processing system may include one or more other types of processors coupled to the processor 104, such as a graphic processing unit (GPU), a tensor processing unit (TPU), a neural processing unit (NPU), an application specific integrated circuit, or a field programmable gate array (FPGA), for offloading certain computing tasks. The processor 104 is coupled to a plurality of components via a communication bus (not shown) which provides a communication path between the components and the processor 104. The processor 104 is coupled to Random Access Memory (RAM) 108, Read Only Memory (ROM) 110, and persistent (non-volatile) memory 112 such as flash memory and a communication subsystem 130.

The communication subsystem 130 includes one or more wireless transceivers for exchanging radio frequency signals with wireless networks. The communication subsystem 130 may also include a wireline transceiver for wireline communications with wired networks. The wireless transceivers may include one or a combination of Bluetooth transceiver or other short-range wireless transceiver, a Wi-Fi or other wireless local area network (WLAN) transceiver for communicating with a WLAN via a WLAN access point (AP), or a wireless wide area network (WWAN) transceiver such as a cellular transceiver for communicating with a radio access network (e.g., cellular network). The cellular transceiver may communicate with any one of a plurality of fixed transceiver base stations of the cellular network within its geographic coverage area. The wireless transceivers may include a multi-band cellular transceiver that supports multiple radio frequency bands. Other types of short-range wireless communication include near field communication (NFC), IEEE 802.15.3a (also referred to as UltraWideband (UWB)), Z-Wave, ZigBee, ANT/ANT+ or infrared (e.g., Infrared Data Association (IrDA) communication). The wireless transceivers may include a satellite receiver for receiving satellite signals from a satellite network that includes a plurality of satellites which are part of a global or regional satellite navigation system.

The wireless device 10 also comprises a microphone 132 and a speaker 134 coupled to the processor 104. The wireless device 10 may also comprise a camera 136, a touchscreen 138, clock (not shown) and a satellite receiver 140 for receiving satellite signals from a satellite network, depending on the type of the wireless device 10. The touchscreen 138 is typically a capacitive touchscreen. The wireless device 10 may also comprise a plurality of sensors 120 coupled to the processor 104. The sensors 120 may comprise a biometric sensor 122 such as face scanner or finger print scanner, a motion sensor 124 such as an accelerometer, an infrared (IR) sensor 126, and/or a proximity sensor 128. The sensors 120 may include other sensors (not shown) such as an orientation sensor, electronic compass or altimeter, among possible embodiments. The wireless device 10 may also comprise one or more other input devices 142 such as buttons, switches, dials, a keyboard or keypad, or navigation tool, depending on the type of the wireless device 10.

Operating system software 150 executable by the processing system, including the processor 104 is stored in the persistent memory 112 but may be stored in other types of memory devices, such as ROM 108 or similar storage element. The operating system software 150 provides a visual user interface (VUI) for user interaction with the wireless device 10 in the form of touch inputs detected via the touchscreen 138 and/or other input devices 142. A number of application programs 158 executable by the processing system, including the processor 104 are also stored in the persistent memory 112. The application programs 158 comprises a contact tracing application 160. Alternatively, the contact tracing application 160 may be part of the operating system software 150 or an application programming interface (API). The contact tracing application 160 comprises instructions for enabling contact tracing in accordance with the teachings of the present disclosure, such as the method 400 described below.

APIs or other extensions of the contact tracing application 160 enable subroutines or functions of the contact tracing application 160 to be performed when the contact tracing application 160 is not the active or foreground application. The contact tracing application 160 is configured to periodically receive from the server 30 contact information of users in the form of diagnosis keys who have tested positive for an infectious disease in one or more geographic regions designated by the user even when the contact tracing application 160 is not the active or foreground application. In response to receiving contact information for positive users, the contact tracing application 160 determines RPIs for the positive users and compares the contact information in the form of RPIs for the positive users with contact information in the form of RPIs for other users with whom the user has been in contact that is stored locally on the wireless device 10 and generates a notification on the wireless device 10 in response to a match being found. The contact tracing application 160 is also configured to exchange contact information in the form of RPIs to track contacts as described below when the contact tracing application 160 is not the active or foreground application.

The memory 112 stores a variety of data 172, including sensor data acquired by the plurality of sensors 120, including sensor data acquired by the biometric sensor 122, sensor data acquired by the motion sensor 124 (i.e. accelerometer, gyroscope, or inertial measurement unit (IMU) of the wireless device 10), sensor data acquired by the infrared sensor 126, and sensor data acquired by the proximity sensor 128. The memory 112 also stores location data 174 about the location of the wireless device 10 over time, tracing keys 176 (including the permanent tracing key, daily tracing keys, and RPIs) used by the contact tracing application 160, input data acquired by the touchscreen 138 and/or other input devices 142, user data including user preferences, settings and possibly biometric data about the user for authentication and/or identification, a download cache including data downloaded via the wireless transceivers, and saved files. System software, software modules, specific device applications, or parts thereof, may be temporarily loaded into RAM 108. Communication signals received by the wireless device 10 may also be stored in RAM 108. Although specific functions are described for various types of memory, this is merely one embodiment, and a different assignment of functions to types of memory may be used in other embodiments.

The wireless device 10 may also comprise a battery (not shown) as a power source, such as one or more rechargeable batteries that may be charged, for example, through charging circuitry coupled to a battery interface such as the serial data port. The battery provides electrical power to at least some of the components of the wireless device 10, and the battery interface (not shown) provides a mechanical and electrical connection for the battery.

Figure 4:
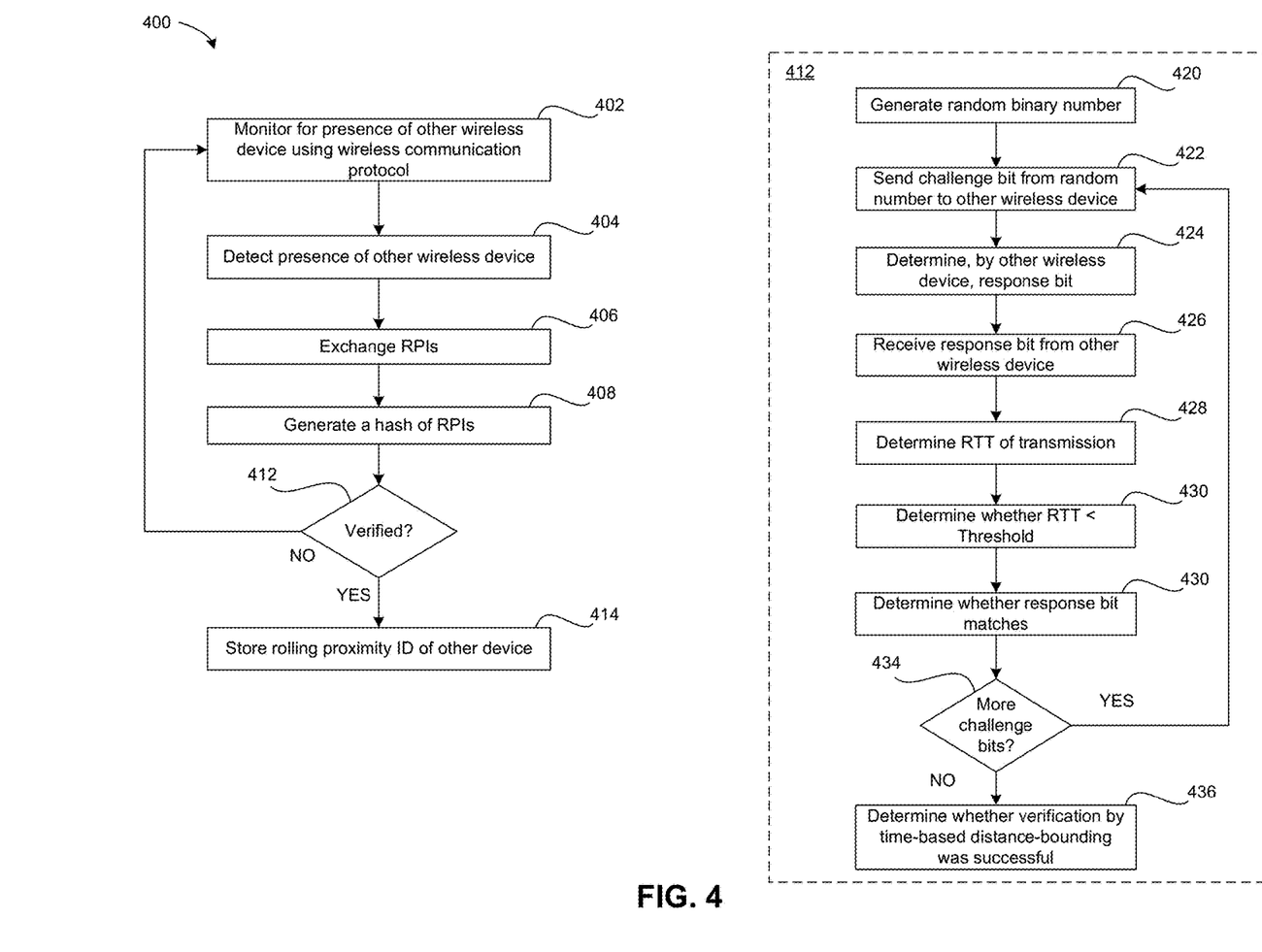
FIG. 4 is flowchart of a method of exchanging identifiers for use in contact tracing application tracing in accordance with an embodiment of the present disclosure.
Figure 5:
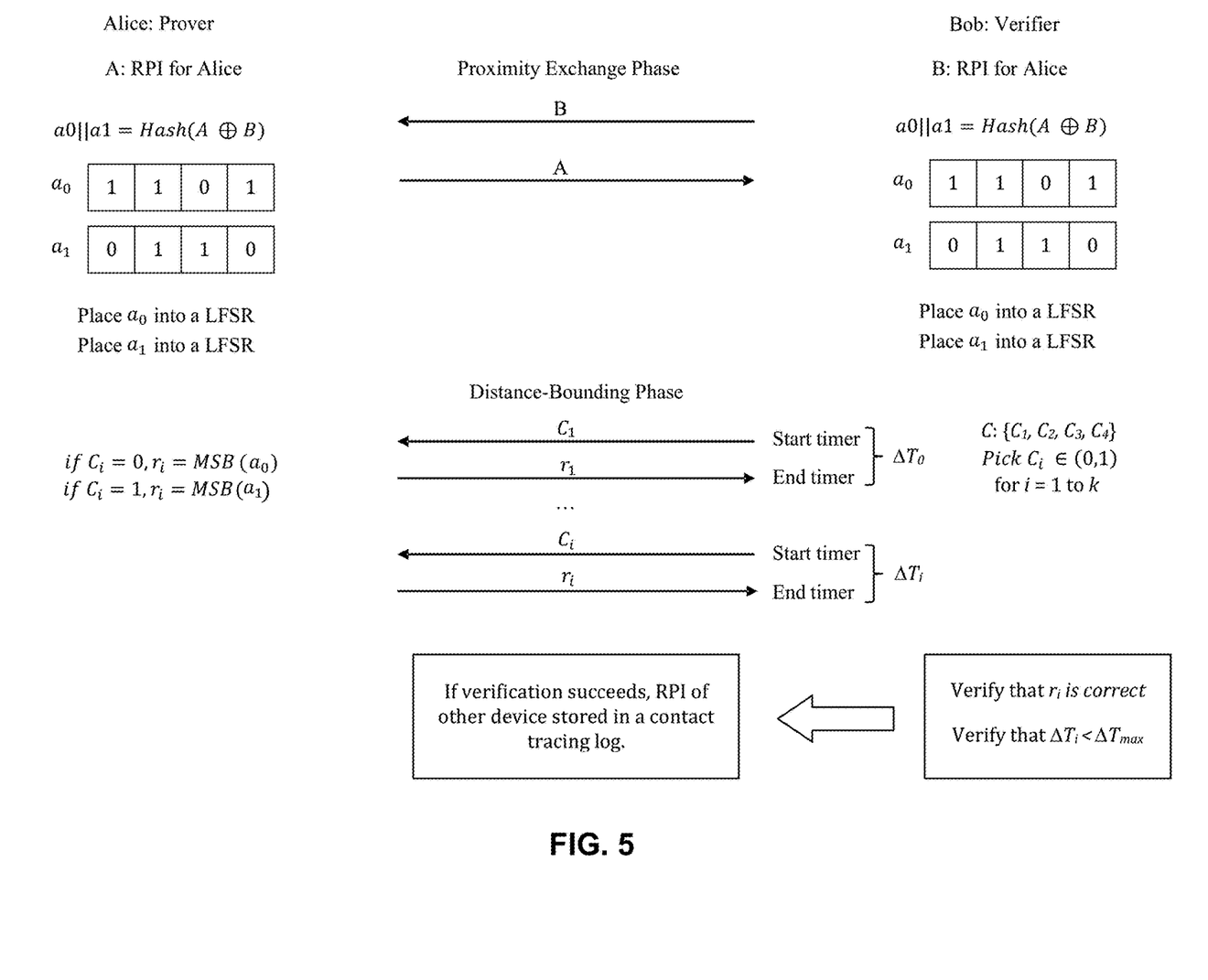
FIG. 5 is a schematic diagram of a message sequence in a method of exchanging identifiers for use in digital contact tracing.

Referring now to FIGS. 4 and 5, a method of exchanging identifiers for use in digital contact tracing will be described. FIG. 4 is a flowchart of a method 400 of exchanging identifiers for use in digital contact tracing in accordance with an example embodiment of the present disclosure. FIG. 5 is a schematic diagram of a message sequence in a method of exchanging identifiers for use in digital contact tracing. At least parts of the method 400 are carried out by software executed by the processor 104 of a wireless device 10, for example, based on the instructions of the contact tracing application 160. For the purposes of illustration, the method will be described at least in part from the perspective of the wireless device 10B of the user Bob.

At operation 402, the wireless device 10B monitors for the presence of other wireless devices 10 using a wireless communication protocol such as Bluetooth™ or Wi-Fi™. A wireless communication protocol other than Bluetooth™ or Wi-Fi™ may be used in other embodiments. Other possible wireless communication protocols may include IEEE 802.11, IEEE 802.15.3a (also referred to as UltraWideband (UWB)), Z-Wave, ZigBee, and infrared (e.g., such as an Infrared Data Association (IrDA) communications).

At operation 404, the wireless device 10B detects the presence of another wireless device 10 in the form of the wireless device 10A of the user Alice. The distance or proximity of the wireless devices to each other for detection depends on the wireless communication protocol and environmental conditions of the location at which the users are present.

At operation 406, the wireless devices 10A and 10B exchange RPIs A and B for users Alice and Bob respectively, in response to the wireless devices 10A and 10B of Alice and Bob being detecting each other via the wireless communication protocol (e.g., Bluetooth™ or Wi-Fi™).

Alternatively, rather than detecting the presence of another wireless device 10 and exchange RPIs in response to the wireless devices 10 detecting each other via the wireless communication protocol in operations 402-406, the wireless devices 10 may receive all RPIs broadcast over the wireless communication protocol and temporarily store in RAM 108.

At operation 408, the wireless devices 10A and 10B each calculate a hash of the RPIs A and B in accordance with a predetermined hash function. In some examples, the hashes are calculated in accordance with the following equation(s):

$$a0 \| a1 = \text{Hash}(A \oplus B)$$

where A and B are the RPIs for the wireless devices 10A and 10B, A⊕B is the concatenation of A and B, Hash is the predetermined hash function such as SHA-256 truncated to 2n bits (e.g., 8 bits), a0 and a1 are the first half of the output bits and the last half of the outputs of the hash function Hash, respectively, wherein a0 and a1 are each n bits long (e.g., 4 bits). In some examples, the hash n is 4 such that a0 and a1 are each 4 bits long. It has been determined that a 4 bit number provides a sufficient number of data points for time-based distance-bounding determinations which are sufficiently accurate and fast for proximity thresholds considered in the present disclosure. However, a different number of bits, such as 8 bits, may be used in other examples.

For purposes of illustration, the wireless devices 10A and 10B output the following values for a0 and a1:

| a0 | 1 | 1 | 0 | 1 |
|---|---|---|---|---|
| a1 | 0 | 1 | 1 | 0 |

At operation 412, the wireless device 10B of the user Bob, in the role of verifier, performs a cryptographic challenge response authentication with time-based distance-bounding on the rolling proximity identifiers A and B to determine whether the hash value can be verified. A distance-bounding protocol is a cryptographic protocol that securely establishes an upper bound on the physical distance between participant devices. The distance-bounding protocol enables a verifier to establish the upper bound on the physical distance to a prover. The time-based distance-bounding protocol is based on timing the delay between sending challenge bits and receiving corresponding response bits. The delay time for responses enables the verifier to compute the upper bound on the distance as the round trip time (RTT) divided into twice the speed of light. The distance bound computed by a radio frequency (RF) time-based distance-bounding protocol is very sensitive to processing delays because any delay introduced anywhere in the system will be multiplied by approximately the speed of light to convert time into distance. Because of the extremely tight timing constraints and the time-based distance-bounding requires that the prover apply an appropriate check function to the challenge sent by the verifier, it is non-trivial to implement time-based distance-bounding in physical hardware. If the hash value can be verified with time-based distance-bounding, the wireless devices 10A and 10B are within a predetermined proximity threshold. If the hash value cannot be verified with time-based distance-bounding, the wireless devices 10A and 10B are outside the predetermined proximity threshold.

At operation 414, in response to a successful cryptographic challenge response authentication (e.g., a determination by the wireless device 10B of user Bob that the hash value had been verified with time-based distance-bounding), the RPIs are stored in persistent memory 112 on the wireless devices 10A and 10B. Only one of the wireless devices 10A and 10B perform cryptographic challenge response authentication in the present embodiment, however both of the wireless devices 10A and 10B may perform cryptographic challenge response authentication in other embodiments. When both of the wireless devices 10A and 10B perform cryptographic challenge response authentication, one-end or dual-end verification may be used. In one-end verification, the exchange is aborted when either one of the wireless devices 10A and 10B determine that the hash value cannot be verified with time-based distance-bounding (e.g., in response to an unsuccessful cryptographic challenge response authentication). In dual-end verification, the exchange is aborted when both the wireless devices 10A and 10B determine that the hash value cannot be verified with time-based distance-bounding (e.g., in response to an unsuccessful cryptographic challenge response authentication).

The wireless devices 10A and 10B may store the received RPIs in a contact tracing log. The wireless devices 10A and 10B keep the RPIs for at least a predetermined amount of time, such as between 7 and 21 days, in some examples 14 days. The predetermined amount of time may be based on, or set by, a public health authority. A log of received RPIs may be maintained by the wireless devices 10A and 10B. Although not shown, the RPIs and corresponding log entries (if any) may be removed (or deleted) from persistent memory 112 after the expiry of the predetermined amount of time from at a time at which the RPIs were stored (or received), thereby enhancing the privacy of third parties by purging RPIs when no longer required.

Returning to operation 412, in response to an unsuccessful cryptographic challenge response authentication (e.g., in response to a determination by the wireless device 10B of user Bob that the hash value was not been verified), the RPIs are not stored because the wireless devices 10A and 10B are outside the predetermined proximity threshold, and processing returns to operation 402. The wireless devices 10 refrain from storing the RPIs in response to an unsuccessful cryptographic challenge response authentication.

Returning to operation 412, the cryptographic challenge response authentication and the verification of the hash value with time-based distance-bounding will be described in more detail. As noted above, one of the wireless devices 10A and 10B acts as a verifier and the other of the wireless devices 10A and 10B acts as a prover. The wireless device 10 which acts as a verifier and the wireless device 10 which acts as the prover may be determined randomly or other suitable selection mechanism such as the lowest (or highest) RPI, a round robin algorithm, etc. In the present example, the wireless device 10B of user Bob acts as a verifier and the wireless devices 10A of user Alice acts as a prover for purposes of illustration.

At operation 420, the wireless device 10B generates a 4-bit random binary number denoted C, where C: $\{C_1, C_2, C_3, C_4\}$, where $C_i \in (0,1)$. Each bit in the random binary number C represents a challenge bit. For purposes of illustration, the wireless device 10B generates the following value for C:

| C | 1 | 0 | 0 | 1 |
|---|---|---|---|---|

The value of each challenge bit $C_i$ in the 4-bit random binary number C is then verified by the verifier, i.e. wireless device 10B as described below.

At operation 422, the wireless device 10B associated with user Bob sends challenge bit $C_i$ to wireless device 10A associated with user Alice, which is subsequently received by the wireless device 10A.

At operation 426, the wireless device 10A associated with user Alice the wireless device 10B generates a response bit $r_i$ based on the challenge bit $C_i$. If $C_i=0$, the response bit $r_i=MSB(a_0)$, where MSB denotes the most significant bit. If $C_i=1$, the response bit $r_i=MSB(a_1)$.

At operation 426, the wireless device 10A associated with user Alice sends the response bit $r_i$ to wireless device 10B associated with user Bob, which is subsequently received by the wireless device 10B.

At operation 428, the wireless device 10B associated with user Bob measures, or determines, the RTT of each transmission, denoted $\Delta T_i$. Each transmission begins with the sending of the challenge bit $C_i$ and ends with the receiving of the response bit $r_i$. The wireless device 10B may user a timer to determine the RTT or may determine the RTT based on a clock time based on the time at which the challenge bit $C_i$ was sent and the time at which the response bit $r_i$ was received, which are associated with respective time stamps by the processor 104.

At operation 430, the wireless device 10B associated with user Bob determines whether $\Delta T_i < T_{max}$, where $T_{max}$ is a predetermined time threshold calculated based on a predetermined proximity threshold. The predetermined proximity threshold based on a physical or social distance recommended by public health authorities, such as between 3 and 6 feet or between 1 and 2 m. The value $T_{max}$ is based on the RTT for the predetermined proximity threshold. When the predetermined proximity threshold is 2 m, the RTT is 13.34256381 nanoseconds or 0.013342564 milliseconds (ms). The value of $T_{max}$ is based on RTT plus a computation allowance for determining the response bit $r_i$, input/output processing of the prover and verifier and an tolerance. Depending on the hardware of the prover and verifier, the value of $T_{max}$ may be 1 ms or less, possibly 0.1 ms or less. The value of $T_{max}$ is set based on the predetermined proximity threshold to reduce the false readings to within an acceptable level.

At operation 432, the wireless device 10B associated with user Bob determines whether the response bit $r_i$ matches the expectations based on the challenge bit, i.e. $r_i=MSB(a_0)$ when $C_i=0$ and $r_i=MSB(a_1)$ when $C_i=1$.

The operations 422-432 are performed for each challenge bit $C_i$ in the 4-bit random binary number C. After each challenge bit has been evaluated, the wireless device 10B determines whether there any remaining challenge bits that have yet to be evaluated (decision block 434). If there are challenge bits remaining, processing returns to operation 422. The wireless device 10B may input a0 and a1 into a left shift register which shifts the values of a0 and a1 left by 1 bit respectively.

If there are no challenge bits remaining, processing proceeds to operation 436 at which it is determined whether verification with time-based distance-bounding was successful. If the RTT ($\Delta T_i$) exceeds the predetermined time threshold ($T_{max}$) or response bit does not match the challenge bit for any challenge bit $C_i$ in the 4-bit random binary number C, the verification of the hash value with time-based distance-bounding fails. The determination of whether the hash value with time-based distance-bounding has been verified is made after all challenge bits have been evaluated in the present embodiment. In other embodiments, the determination of whether the hash value with time-based distance-bounding has been verified after each of the checks in operations 430 and 432 for a given challenge bit so that the verification with time-based distance-bounding is determined to have failed immediately after it has been determined that the RTT ($\Delta T_i$) exceeds the predetermined time threshold ($T_{max}$) or response bit does not match the challenge bit for any challenge bit $C_i$ in the 4-bit random binary number. In an alternative embodiment, the determination of whether the hash value with time-based distance-bounding has been verified after both the checks in operations 430 and 432 for a given challenge bit.

In another alternative embodiment, the total RTT of all transmissions may be considered rather than the RTT of individual transmissions.

Although in the example embodiments above, only one of the wireless devices 10A and 10B, both the of wireless devices 10A and 10B may act as verifier and prover in turn, with the RPI of the other wireless device only being stored in response to both of the wireless devices 10A and 10B having verified the hash value. In response a determination that more than two wireless devices are in proximity to each other, the method 400 is performed between each respective pair of wireless devices 10.

The method of the present disclosure provides a proximity-based exchange of identifiers with time-based distance-bounding which provides several advantageous. Firstly, the method is air interface neutral, meaning it can be used with Bluetooth™, Wi-Fi™, or both, and potentially other wireless communication protocols. Existing solutions rely upon Bluetooth™ or GPS for proximity discovery means. Secondly, the method provides privacy protection by anonymizing the identifier exchanged. Thirdly, the method protects against various attacks including man-in-the-middle attacks, replay attacks, forgery attacks, and pranking attacks. Lastly, the method reduces false positive readings of disease-communicable contact by ensuring the precision of distance at which proximity is detected, a distance of approximately 10 meters or less (e.g., between 3 and 6 feet or between 1 and 2 m in some examples) in the method of the present disclosure compared with a distance of approximately 100 m or less with existing solutions.

General

The steps and/or operations in the flowcharts and drawings described herein are for purposes of example only. There may be many variations to these steps and/or operations without departing from the teachings of the present disclosure. For instance, the steps may be performed in a differing order, or steps may be added, deleted, or modified, as appropriate.

The coding of software for carrying out the above-described methods described is within the scope of a person of ordinary skill in the art having regard to the present disclosure. Machine-readable code executable by one or more processors of one or more respective devices to perform the above-described method may be stored in a machine-readable medium such as the memory of the data manager. The terms "software" and "firmware" are interchangeable within the present disclosure and comprise any computer program stored in memory for execution by a processor, comprising Random Access Memory (RAM) memory, Read Only Memory (ROM) memory, EPROM memory, electrically EPROM (EEPROM) memory, and non-volatile RAM (NVRAM) memory. The above memory types are examples only, and are thus not limiting as to the types of memory usable for storage of a computer program.

All values and sub-ranges within disclosed ranges are also disclosed. Also, although the systems, devices and processes disclosed and shown herein may comprise a specific plurality of elements, the systems, devices and assemblies may be modified to comprise additional or fewer of such elements. Although several example embodiments are described herein, modifications, adaptations, and other implementations are possible. For example, substitutions, additions, or modifications may be made to the elements illustrated in the drawings, and the example methods described herein may be modified by substituting, reordering, or adding steps to the disclosed methods.

Features from one or more of the above-described embodiments may be selected to create alternate embodiments comprised of a subcombination of features which may not be explicitly described above. In addition, features from one or more of the above-described embodiments may be selected and combined to create alternate embodiments comprised of a combination of features which may not be explicitly described above. Features suitable for such combinations and subcombinations would be readily apparent to persons skilled in the art upon review of the present disclosure as a whole.

In addition, numerous specific details are set forth to provide a thorough understanding of the example embodiments described herein. It will, however, be understood by those of ordinary skill in the art that the example embodiments described herein may be practiced without these specific details. Furthermore, well-known methods, procedures, and elements have not been described in detail so as not to obscure the example embodiments described herein. The subject matter described herein and in the recited claims intends to cover and embrace all suitable changes in technology.

Although the present disclosure is described at least in part in terms of methods, a person of ordinary skill in the art will understand that the present disclosure is also directed to the various elements for performing at least some of the aspects and features of the described methods, be it by way of hardware, software or a combination thereof. Accordingly, the technical solution of the present disclosure may be embodied in a non-volatile or non-transitory machine-readable medium (e.g., optical disk, flash memory, etc.) having stored thereon executable instructions tangibly stored thereon that enable a processing device to execute examples of the methods disclosed herein.

The term "database" may refer to either a body of data, a relational database management system (RDBMS), or to both. As used herein, a database may comprise any collection of data comprising hierarchical databases, relational databases, flat file databases, object-relational databases, object oriented databases, and any other structured collection of records or data that is stored in a computer system. The above examples are example only, and thus are not intended to limit in any way the definition and/or meaning of the terms "processor" or "database".

The present disclosure may be embodied in other specific forms without departing from the subject matter of the claims. The described example embodiments are to be considered in all respects as being only illustrative and not restrictive. The present disclosure intends to cover and embrace all suitable changes in technology. The scope of the present disclosure is, therefore, described by the appended claims rather than by the foregoing description. The scope of the claims should not be limited by the embodiments set forth in the examples, but should be given the broadest interpretation consistent with the description as a whole.

The invention claimed is:

1. A method performed by a first wireless communication device for exchanging identifiers (ID) with a second wireless communication device, comprising:
   sending a rolling proximity identifier A associated with the first wireless communication device to the second wireless communication device;
   receiving a rolling proximity identifier B associated with the second wireless communication device from the second wireless communication device;
   performing a cryptographic challenge response authentication with time-based distance-bounding on the rolling proximity identifiers A and B, wherein the cryptographic challenge response authentication with time-based distance-bounding is based on a hash value determined from the rolling proximity identifier A and the rolling proximity identifier B in accordance with a hash function, wherein the cryptographic challenge response authentication with time-based distance-bounding comprises:
      determining the hash value based on the rolling proximity identifier A and the rolling proximity identifier B in accordance with the hash function;
      generating a challenge bit;
      sending the challenge bit to the second wireless communication device;
      receiving a response bit from the second wireless communication device;

determining whether the response bit matches the corresponding challenge bit in accordance with a check function;

determining whether a round trip time for the challenge-response transmission exceeds a time threshold, wherein the time threshold is based on a proximity threshold, wherein the transmission begins with sending a challenge bit and ends with receiving a response bit;

determining that the hash value has been verified in response to a determination that the round trip time for the challenge-response transmission does not exceed the time threshold and a determination that the response bit matches the challenge bit; and determining that the hash value has not been verified in response to a determination that the round trip time for the challenge-response transmission exceeds the time threshold or a determination that the response bit does not match the challenge bit; and storing the rolling proximity identifier B in memory in response to a successful cryptographic challenge response authentication.

2. The method of claim 1, wherein the rolling proximity identifiers are exchanged using a first wireless communication protocol.

3. The method of claim 1, further comprising, after storing the rolling proximity identifier B in memory:

determining whether an amount of time has expired from a time at which the rolling proximity identifier B of the second wireless communication device was stored; and removing the rolling proximity identifier B of the second wireless communication device from memory in response to a determination that the amount of time has expired.

4. The method of claim 3, wherein the amount of time is an amount of isolation time set by a public health authority.

5. The method of claim 3, wherein the amount of time is between 7 and 21 days.

6. The method of claim 1, further comprising refraining from storing the rolling proximity identifier B in memory in response to an unsuccessful cryptographic challenge response authentication.

7. The method of claim 1, wherein the hash function is performed on a concatenation of A and B, wherein the output of the hash function is truncated to 2n bits, wherein a0 is the first half of the output bits of the hash function, wherein a0 and a1 are each n bits in size.

8. The method of claim 7, wherein the response bit is based on the challenge bit, wherein the response bit has a value equal to a most significant bit of a0 when the challenge bit has a value of 0 and the response bit has a value equal to a most significant bit of a1 when the challenge bit has a value of 1.

9. The method of claim 7, wherein n is 4 such that a0 and a1 are each 4 bits in size.

10. The method of claim 1, wherein the cryptographic challenge response authentication with time-based distance-bounding comprises:

determining the hash value based on the rolling proximity identifier A and the rolling proximity identifier B in accordance with the hash function;

generating an n-bit random binary number C, where C: $\{C_1, C_2, \ldots C_n\}$, where $C_i \in (0,1)$, wherein each bit in the random binary number C represents a challenge bit;

for each bit in the random binary number C:
sending a challenge bit to the second wireless communication device;

receiving a response bit from the second wireless communication device;

determining a round trip time for the challenge-response transmission beginning with the sending of the challenge bit and ending with the receiving of the response bit;

determining whether the round trip time exceeds a time threshold, wherein the time threshold is based on a proximity threshold, and determining whether the response bit matches the challenge bit in accordance with a check function based on the hash value;

determining that the hash value has been verified in response to a determination that the round trip time for the challenge-response transmission does not exceed the time threshold and a determination that the response bit matches the challenge for each challenge bit in the random binary number C; and determining that the hash value has not been verified in response to a determination that the round trip time for the challenge-response transmission exceeds the time threshold or a determination that the response bit does not match the challenge bit for any challenge bit in the random binary number C.

11. The method of claim 10, wherein the proximity threshold is a physical or social distance set by a public health authority.

12. The method of claim 10, wherein the proximity threshold is between 3 and 6 feet or between 1 and 2 m.

13. The method of claim 10, wherein the hash function is performed on a concatenation of A and B, wherein the output of the hash function is truncated to 2n bits, wherein a0 is the first half of the output bits of the the hash function, wherein a0 and a1 are each n bits in size.

14. The method of claim 13, wherein the response bit is based on the challenge bit, wherein the response bit has a value equal to a most significant bit of a0 when the challenge bit has a value of 0 and the response bit has a value equal to a most significant bit of a1 when the challenge bit has a value of 1.

15. The method of claim 13, wherein the hash function is SHA-256, wherein the output of the SHA-256 hash function is truncated to 2n bits.

16. The method of claim 13, wherein n is 4 such that a0, a1 and the random binary number C are each 4 bits in size.

17. The method of claim 2, wherein the first wireless communication protocol is Bluetooth or Wi-Fi.

18. A first wireless communication device, comprising:
a processor;
a communication subsystem coupled to the processor;
a memory coupled to the processor;
wherein the processor is configured to:
send a rolling proximity identifier A associated with the first wireless communication device to the second wireless communication device;
receive a rolling proximity identifier B associated with the second wireless communication device from the second wireless communication device;
perform a cryptographic challenge response authentication with time-based distance-bounding on the rolling proximity identifiers A and B, wherein the cryptographic challenge response authentication with time-based distance-bounding is based on a hash value determined from the rolling proximity identifier A and the rolling proximity identifier B in accordance with a hash function, wherein the cryptographic challenge response authentication with time-based distance-bounding comprises:
determining the hash value based on the rolling proximity identifier A and the rolling proximity identifier B in accordance with the hash function;
generating a challenge bit;
sending the challenge bit to the second wireless communication device;
receiving a response bit from the second wireless communication device;
determining whether the response bit matches the corresponding challenge bit in accordance with a check function;
determining whether a round trip time for the challenge-response transmission exceeds a time threshold, wherein the time threshold is based on a proximity threshold, wherein the transmission begins with sending a challenge bit and ends with receiving a response bit;
determining that the hash value has been verified in response to a determination that the round trip time for the challenge-response transmission does not exceed the time threshold and a determination that the response bit matches the challenge bit; and
determining that the hash value has not been verified in response to a determination that the round trip time for the challenge-response transmission exceeds the time threshold or a determination that the response bit does not match the challenge bit; and
store the rolling proximity identifier B in memory in response to a successful cryptographic challenge response authentication.

19. A non-transitory machine-readable medium having tangibly stored thereon executable instructions for execution by a processor of a first wireless communication device, wherein the executable instructions, in response to
send a rolling proximity identifier A associated with the first wireless communication device to the second wireless communication device;
receive a rolling proximity identifier B associated with the second wireless communication device from the second wireless communication device;
perform a cryptographic challenge response authentication with time-based distance-bounding on the rolling proximity identifiers A and B, wherein the cryptographic challenge response authentication with time-based distance-bounding is based on a hash value determined from the rolling proximity identifier A and the rolling proximity identifier B in accordance with a hash function, wherein the cryptographic challenge response authentication with time-based distance-bounding comprises:
determining the hash value based on the rolling proximity identifier A and the rolling proximity identifier B in accordance with the hash function;
generating a challenge bit;
sending the challenge bit to the second wireless communication device;
receiving a response bit from the second wireless communication device;
determining whether the response bit matches the corresponding challenge bit in accordance with a check function;
determining whether a round trip time for the challenge-response transmission exceeds a time threshold, wherein the time threshold is based on a proximity threshold, wherein the transmission begins with sending a challenge bit and ends with receiving a response bit;
determining that the hash value has been verified in response to a determination that the round trip time for the challenge-response transmission does not exceed the time threshold and a determination that the response bit matches the challenge bit; and
determining that the hash value has not been verified in response to a determination that the round trip time for the challenge-response transmission exceeds the time threshold or a determination that the response bit does not match the challenge bit; and
store the rolling proximity identifier B in memory in response to a successful cryptographic challenge response authentication.

* * * * *

UNITED STATES PATENT AND TRADEMARK OFFICE
CERTIFICATE OF CORRECTION

PATENT NO. : 11,764,980 B2  
APPLICATION NO. : 17/246421  
DATED : September 19, 2023  
INVENTOR(S) : Sheng Sun and Wen Tong Page 1 of 1

It is certified that error appears in the above-identified patent and that said Letters Patent is hereby corrected as shown below:

In the Specification

Column 3, Line 41. Replace "0.30 and a1 are each 4 bits in size."  
With -- a0 and a1 are each 4 bits in size. --.

Column 3, Line 47. Replace "generating an n-bit random binary number C, where {C1,"  
With -- generating an n-bit random binary number C, where C: {C1 --.

In the Claims

Column 18, Line 34 (Claim 13). Replace "first half of the output bits of the the hash function, wherein"  
With -- first half of the output bits of the hash function, wherein --.

Signed and Sealed this  
Fourth Day of March, 2025

Coke Morgan Stewart  
*Acting Director of the United States Patent and Trademark Office*